(12) United States Patent
Igarashi et al.

(10) Patent No.: US 7,413,886 B2
(45) Date of Patent: Aug. 19, 2008

(54) PROCESS FOR PRODUCING PHOSPHORYLASE

(75) Inventors: Kazuaki Igarashi, Tochigi (JP); Shuuichi Takizawa, Tochigi (JP); Norihiko Higaki, Tochigi (JP); Jun Hitomi, Tochigi (JP)

(73) Assignee: Kao Corporation, Tokyo (JP)

( * ) Notice: Subject to any disclaimer, the term of this patent is extended or adjusted under 35 U.S.C. 154(b) by 170 days.

(21) Appl. No.: 10/558,303

(22) PCT Filed: Jun. 4, 2004

(86) PCT No.: PCT/JP2004/007815

§ 371 (c)(1),
(2), (4) Date: Nov. 28, 2005

(87) PCT Pub. No.: WO2004/108913

PCT Pub. Date: Dec. 16, 2004

(65) Prior Publication Data

US 2006/0234341 A1   Oct. 19, 2006

(30) Foreign Application Priority Data

Jun. 6, 2003   (JP) ............................. 2003-162397

(51) Int. Cl.
*C12N 9/12* (2006.01)
*C12N 1/20* (2006.01)
*C12N 1/02* (2006.01)
*C12P 21/04* (2006.01)

(52) U.S. Cl. ............... 435/194; 435/71.1; 435/252.32; 435/252.1; 435/261

(58) Field of Classification Search ................ None
See application file for complete search history.

(56) References Cited

FOREIGN PATENT DOCUMENTS

| | | |
|---|---|---|
| FR | 2547593 A1 | 12/1984 |
| JP | 1-91778 A | 4/1989 |
| JP | 3-4785 A | 1/1991 |
| JP | 8-280382 A | 10/1996 |
| JP | 10-14580 A | 1/1998 |
| JP | 10-276785 A | 10/1998 |
| JP | 2-154686 A | 12/1998 |
| JP | 10-327887 A | 12/1998 |
| JP | 11-89566-1 | 4/1999 |
| JP | 2002-345458 A | 12/2002 |

OTHER PUBLICATIONS

Dols et al. (1997) Appl. Environ. Microbiol. 63(6): 2159-2165.*
Koga et al. (1991) Agric. Biol. Chem. 55(7): 1805-1810.*
Kitao et al., J. of Fermentation and Bioengineering, vol. 73, No. 3, pp. 179-184, (1992).
English Language Abstract of JP 2000 004670 A (Jan. 11, 2000).

* cited by examiner

*Primary Examiner*—Lisa J Hobbs
(74) *Attorney, Agent, or Firm*—Birch, Stewart, Kolasch & Birch, LLP

(57) ABSTRACT

It is intended to provide a process for conveniently producing phosphorylase at a high purity using a phosphorylase-producing microorganism. Namely, a process for producing phosphorylase characterized by culturing a phosphorylase-producing microorganism in a medium containing phosphoric acid or its salt at a concentration of 50 mM or above and collecting the phosphorylase thus produced in the medium.

9 Claims, No Drawings

PROCESS FOR PRODUCING PHOSPHORYLASE

FIELD OF THE INVENTION

The present invention relates to a process for producing phosphorylase using a phosphorylase-producing microorganism.

BACKGROUND OF THE INVENTION

Phosphorylase is an enzyme which catalyzes phosphorolysis of the substrate saccharide in the presence of inorganic phosphoric acid. The phosphorylases are generally named based on the substrate sugar molecule, and include, for example, maltodextrin phosphorylase, sucrose phosphorylase, maltose phosphorylase, cellobiose phosphorylase, trehalose phosphorylase. Such phosphorylases are useful as a reagent for the quantitative assay of the substrate of inorganic phosphoric acid or saccharide, and also useful as an enzyme applicable to the synthesis of various glycosides from phosphorylated saccharide using its catalytic property of reversible phosphorolysis.

Phosphorylases are known to be stored as intracellular enzymes in various microorganisms such as those belonging to genus *Leuconostoc*.

To utilize the phosphorylase for the purpose described above, it is desirable that the purity of the enzyme preparation is increased to some reasonable level. For the purpose of obtaining such enzyme preparation, a phosphorylase producing microorganism is cultured, and after that, several complicated processes such as recovery of the cultured microorganism (cell), washing the cell, lysing the cell, isolation of enzyme fraction, and purification of the enzyme have to be carried out (for example, refer to patent documents 1 to 5). In this process, addition of a lytic enzyme or a chelating agent which is required for cell lysis becomes necessary, and further, almost all the cell components are released; therefore a heavy burden is added onto the enzyme purification process.

As the means to reduce such a load of purification, a method of increasing intracellular phosphorylase level, for example by optimization of the medium composition (for example, refer to patent documents 6 and 7), a method of generating objective phosphorylase with high purity using recombinant microorganisms (for example, refer to non-patent document 1 and patent documents 3 to 5), a method of simplifying the purification process (for example, refer to patent document 8), and the like have been known. However, as the process itself can not be changed, these methods have not provided satisfactory results.

Patent document 1: JP-A-1989-91778
Patent document 2: JP-A-1996-280382
Patent document 3: JP-A-1998-14580
Patent document 4: JP-A-1998-276785
Patent document 5: JP-A-1998-327887
Patent document 6: JP-A-1990-154686
Patent document 7: JP-A-1991-4785
Patent document 8: JP-A-2002-345458
Non-patent document 1: Kitao et al., J. Ferment. Bioeng., 73, 179-184(1992)

SUMMARY OF THE INVENTION

The present invention relates to a process for producing phosphorylase efficiently and easily from a phosphorylase-producing microorganism.

The present inventors have found that the phosphorylase can be produced in a culture medium with high yield when the phosphorylase-producing microorganism is cultured in a medium containing high concentration of phosphoric acid, and the phosphorylase can be obtained efficiently without conducting laborious procedures such as recovery of the enzyme from inside of the cell.

Namely, the present invention is to provide a process for producing phosphorylase, characterized in that a phosphorylase-producing microorganism is cultured in a medium containing 50 mM or higher concentration of phosphoric acids or the salts thereof, and the phosphorylase produced in the medium is collected.

Also, the present invention is to provide a medium for producing phosphorylase, wherein the concentration of the phosphoric acids or the salts thereof in the medium is 50 mM or higher.

According to the present invention, after culturing the phosphorylase-producing microorganism, the phosphorylase can be obtained efficiently and easily by simple processes such as collection of culture supernatant (cell removal) and purification.

BEST MODE FOR CARRYING OUT THE INVENTION

The phosphorylase-producing microorganism to be used in the present invention may be such microorganisms that produce the phosphorylase inside the cell and excretes the phosphorylase in a culture medium when cultured under the specific concentration of phosphoric acids or the salts thereof, which includes microorganisms belonging to genera, for example *Escherichia, Bacillus, Klebsiella, Streptococcus, Corynebacterium, Thermus, Thermococcus, Thermotoga, Leuconostoc, Pseudomonas, Clostridium, Acetobacter, Pullularia, Agrobacterium, Synecoccus, Aspergillus, Monilia, Sclerotinea, Chlamydomonas, Lactobacillus, Neiserria, Enterococcus, Lactococcus, Plesiomonas, Catellatospora, Kineosporia, Micrococcus, Arthrobacter, Brevibacterium, Flavobacterium, Serratia, Streptomyces, Xanthomonas, Thermoanaerobium, Phizopus, Chaetomium, Acreomonium, Byssochilamys, Cercospora, Glomerella, Humicola, Myceliophthora, Rhizomucor, Rosellinia, Sclerotinia, Sporidiobolus, Sterigmatomyces, Thermoascus, Thielavia, Tyromyces, Erwinia, Ruminococcus,* and *Cellvibrio*.

The phosphorylase-producing microorganism may be a mutant strain having increased productivity of the phosphorylase, derived naturally or by UV irradiation or by treatment with chemical mutation inducer such as N-methyl-N'-nitro-N-nitrosoguanidine (MNNG) or ethylmethane sulfonate (EMS) (C. Guhrie & G. R. Fink, Methods in Enzymology vol. 194, pp 273-281 Academic Press Inc.).

Among the genera listed above, *Leuconostoc* and *Corynebacterium* are preferable. Among bacteria belonging to *Leuconostoc* genus, *Leuconostoc mesenteroides, Leuconostoc lactis, Leuconostoc fallax, Leuconostoc citreum, Leuconostoc carnosum, Leuconostoc argetinum* and *Leuconostoc pseudomesenteroides*, and among bacteria belonging to *Corynebacterium* genus, *Corynebacterium glutamicum, Corynebacterium callunae, Corynebacterium hoagii, Corynebacterium vitaeruminis* and *Corynebacterium pilosum*, are more preferable. Among those, *Leuconostoc mesenteroides, Leuconostoc mesenteroides* KSM-SP1 (deposited to Patent Creature Deposition Center of National Institute of Advanced Industrial Science and Technology in Japan with a deposition number of FERM BP-10030) and *Leuconostoc mesenteroides* KSM-SP78 (deposited to Patent Creature Deposition Center of National Institute of Advanced Industrial Science and Technology in Japan as of Apr. 28, 2004 with a deposition number of FERM BP-10044), *Corynebacterium vitaeruminis*, *Corynebacterium glutamicum* KSM-MP669 (deposited to Patent Creature Deposition Center of National Institute of Advanced Industrial Science and Technology in Japan as of Apr. 28, 2004 with a deposition number of FERM BP-10043) are even more preferable.

Production of the phosphorylase may be performed by culture of above described phosphorylase-producing microorganism in a medium containing 50 mM or higher concentration of the phosphoric acids or the salts thereof (a medium for phosphorylase production).

The phosphoric acids or the salts thereof to be added in a medium include, for example, phosphoric acid, metaphosphoric acid, trypoliphosphoric acid, polyphosphoric acid, diphosphoric acid, polymetaphosphoric acid and the salts thereof. The preferable salts of the phosphoric acids are the sodium salts or the potassium salts. More preferable salts of the phosphoric acids include, for example, monobasic potassium phosphate, dibasic potassium phosphate, monobasic sodium phosphate and dibasic sodium phosphate. Combined use of the phosphoric acids and the salts thereof, or the mixed use of several kinds of salts of the phosphoric acids are yet further preferable.

In the terms of effectiveness, the concentration of the phosphoric acids or the salts thereof is generally 50 mM or higher; however, the range from 50 mM to 1.5 M is preferable, from 50 mM to 1 M is more preferable, and from 100 mM to 1 M is even more preferable. In addition, for the bacteria belonging to *Leuconostoc* genus, preferable concentration is in the range from 400 mM to 1.2 M; for the bacteria belonging to *Corynebacterium* genus, preferable concentration is in the rage from 100 mM to 600 mM.

The culture medium to be used in the present invention may be a medium in which the phosphorylase-producing microorganism can grow, which includes for example a liquid medium containing carbon source, nitrogen source, minerals, and vitamins in addition to the above described phosphoric acids and the salts thereof.

The saccharide to be used in the present invention includes monosaccharide, disaccharide, oligosaccharide, and polysaccharide, and may be used in a mixture of 2 or more of above saccharides.

As to the carbon source other than saccharides, the salts of organic acids such as acetates maybe included. The nitrogen source includes, for example, inorganic and organic ammonium salts such as ammonia, ammonium chloride, ammonium sulfate, ammonium nitrate, ammonium carbonate, ammonium phosphate, and ammonium acetate, nitrogen-containing organic substances such as urea, peptone, meat extract, yeast extract, and casein hydrolysate, and amino acids such as glycine, glutamic acid, alanine, and methionine. In the mineral, for example, sodium chloride, ferrous sulfate, magnesium sulfate, manganese sulfate, zinc sulfate, and calcium carbonate are included. These minerals may be used singly or by mixing as needed.

The culture will be carried out at the condition optimized by adjusting pH and temperature under which the microorganism can grow sufficiently. In addition, the culturing method includes shaking culture, anaerobic culture, standing culture and the culture in a fermentation tank. The resting microorganism and the immobilized microorganism can also be utilized as a reactor.

Thus, the phosphorylase may be produced in high yield in the culture supernatant when the phosphorylase-producing microorganism is cultured in a medium containing high concentration of phosphoric acid, and the objective phosphorylase may be obtained easily by collection.

The process for isolating the phosphorylase from culture medium may be performed according to the well known procedures, for example, by combination of procedures such as removal of microorganism from the medium, ultrafiltration, salting-out, ion exchange, hydrophobic chromatography, gel filtration and drying. In case of preparing immobilized enzyme, the phosphorylase can be prepared without conducting laborious procedures as a consequence of its extracellular production.

In addition, the measurement of the resulting phosphorylase activity may be carried out according to the general assay method of phosphorylase activity. The assay method includes for example a method described by Weinhausel (Enzyme Microb. Technol., 17, 140-146 (1995)).

According to the present invention, the phosphorylase can be produced directly outside the cell, so that the phosphorylase can be obtained without requiring laborious treatment such as lysing the cell. Further, as the additives in culture medium is only low molecular weight compound of phosphoric acids, a load of the purification will be reduced significantly, and thus the high purity phosphorylase may be prepared easily.

In addition, by direct addition of the substrates such as disaccharides, oligosaccharides, or polysaccharides together with the phosphoric acids or the salts thereof to the culture medium, the corresponding sugar phosphates can be formed without requiring any specific procedure. Further, by the direct contact of the culture supernatant with both a compound for aglycon and a sugar phosphate, a corresponding glycoside can also be produced without requiring any specific procedure.

EXAMPLES

Example 1

Production of phosphorylase by bacteria belonging to genus *Leuconostoc*

*Leuconostoc mesenteroides* JCM9693 was treated with MNNG to induce mutation (C. Guhrie & G. R. Fink, Methods in Enzymology vol. 194, pp 273-281 Academic Press Inc.), and two phosphorylase-producing mutant strains with high productivity, *Leuconostoc mesenteroides* KSM-SP1 (FERM BP-10030) and *Leuconostoc mesenteroides* KSM-SP78 (FERM BP-10044), were obtained. *Leuconostoc mesenteroides* JCM9693, *Leuconostoc carnosum* JCM9695, *Leuconostoc argentinum* JCM11052, *Leuconostoc pseudomesenteroides* JCM11045, *Leuconostoc mesenteroides* KSM-SP1, and *Leuconostoc mesenteroides* KSM-SP78 were each spreaded on a MR Agar medium (Oxoid Ltd.), and cultured at 30° C. under anaerobic condition. One platinum loop of each bacterial culture was inoculated into a liquid medium (containing 1% of yeast extract (Difco Laboratories Inc.), 1% of polypeptone (Nihon Pharmaceutical Co.), 0.04% of magnesium sulfate heptahydrate, 0.02% of manganese chloride tetrahydrate, 0.0002% of ferric sulfate tetrahydrate, 400, 800 or 1000 mM phosphate buffer, 5%, 10% or 15% of sucrose), and cultured by standing at 30° C. for 2 days. The cell was centrifuged off and the culture supernatant was assayed for sucrose phosphorylase activity.

The sucrose phosphorylase activity was assayed by a partially modified Weinhausel's method (Enzyme Microb. Technol., 17, 140-146 (1995)). In a 96-well microplate, 20 μl sample of appropriately diluted culture supernatant was added with 180 µl of enzyme reaction solution (containing 200 mM potassium phosphate buffer (pH 7.0), 90 mM sucrose, 100 mM Tris-acetate buffer (pH 6.8), 2 mM EDTA, 10 mM magnesium sulfate, 2 mM NAD, 10 µM glucose-1,6-diphosphate, 1.2 unit/ml of phosphoglucomutase (derived from rabbit muscle, Roche Diagnostics Systems Inc.), 1.2 unit/ml of glucose-6-phosphate dehydrogenase (derived from *Leuconostoc mesenteroides*, Roche Diagnostics Systems Inc.)), and the increase of absorbance at 340 nm corresponding to the generation of glucose-1-phosphate (G1P) was measured at 37° C. One unit (1 U) of the enzyme was defined as the activity which generates 1µ mole of G1P in 1 minute. The results were shown in Table 1.

TABLE 1

Extracellular sucrose phosphorylase activity (U/L)

| Bacterial strain | Sucrose (%) | Phosphoric acid (mM) | | |
|---|---|---|---|---|
| | | 400 | 800 | 1000 |
| L. mesenteroides JCM9693 | 5 | 206.6 | 709.2 | 720.3 |
| L. mesenteroides JCM9693 | 10 | 8.4 | 573.8 | 606.4 |
| L. mesenteroides JCM9693 | 15 | 0 | 525.4 | 333.8 |
| L. mesenteroides KSM-SP1 | 5 | 3496 | — | — |
| L. mesenteroides KSM-SP78 | 5 | 4355 | — | — |
| L. carnosum JCM9695 | 5 | 130 | — | — |
| L. argentinum JCM11052 | 5 | 155 | — | — |
| L. pseudomesenteroides JCM11045 | 5 | 1154 | — | — |

As apparent from the results shown in Table 1, it was confirmed that the extracellular production of phosphorylase was increased by the increase of phosphoric acid concentration in the medium.

Example 2

Production of phosphorylase by bacteria belonging to genus *Corynebacterium*

*Corynebacterium glutamicum* JCM1321 was treated with MNNG to induce mutation, and a phosphorylase-producing mutant with high productivity, *Corynebacterium glutamicum* KSM-MP669 (FERM BP-10043), was obtained. *Corynebacterium vitaeruminis* JCM1323, *Corynebacterium callunae* IFO15359, *Corynebacterium glutamicum* JCM1321, and *Corynebacterium glutamicum* KSM-MP669 were each spreaded on a SCD Agar medium (Nihon Pharmaceutical Co.), and cultured at 30° C. One platinum loop of each bacterial culture was inoculated into a liquid medium (containing 0.67% of Yeast Nitrogen Base (Difco Laboratories Inc.), 50, 100 or 200 mM phosphate buffer (pH 7), and 15% of dextrin (derived from potato, Sigma)), and cultured by shaking at 30° C. for 6 days. The cell was centrifuged off and the culture supernatant was assayed for maltodextrin phosphorylase activity.

The maltodextrin phosphorylase activity was assayed by a partially modified Weinhausel's method (Enzyme Microb. Technol., 17, 140-146 (1995)). In a 96-well microplate, 20 µl sample of appropriately diluted culture supernatant was added with 180 µl of enzyme reaction solution (containing 200 mM potassium phosphate buffer (pH 7.0), 2% dextrin, 100 mM Tris-acetate buffer (pH 6.8), 2 mM EDTA, 10 mM magnesium sulfate, 2 mM NAD, 10 µM glucose-1,6-diphosphate, 1.2 unit/ml of phosphoglucomutase (derived from rabbit muscle, Roche Diagnostics Systems Inc.), 1.2 unit/ml of glucose-6-phosphate dehydrogenase (derived from *Leuconostoc mesenteroides*, Roche Diagnostics Systems Inc.)), and the increase of absorbance at 340 nm corresponding to the generation of glucose-1-phosphate (G1P) was measured at 37° C. One unit (1 U) of the enzyme was defined as the activity which generates 1µ mole of G1P in 1 minute. The results were shown in Table 2.

TABLE 2

Extracellular maltodextrin phosphorylase activity (U/L)

| Bacterial strain | Phosphoric acid (mM) | | |
|---|---|---|---|
| | 50 | 100 | 200 |
| C. vitaeruminis JCM1323 | 7.1 | 134.0 | 90.3 |
| C. callunae IFO15359 | 0 | 3.6 | 42 |
| C. glutamicum JCM1321 | 0 | 1 | 0.5 |
| C. glutamicum KSM-MP669 | 4.5 | 5.1 | 6.5 |

As apparent from the results shown in Table 2, it was confirmed that the extracellular production of phosphorylase was increased by the increase of phosphoric acid concentration in the medium.

The invention claimed is:

1. A process for producing phosphorylase, which comprises:
   culturing a phosphorylase-producing microorganism in a medium comprising 50 mM or higher concentration of phosphoric acids or the salts thereof, and
   collecting the phosphorylase produced in the medium,
   wherein the phosphorylase-producing microorganisms are bacteria belonging to genus *Leuconostoc* or genus *Corynebacterium*, and
   wherein the phosphorylase is selected from at least one of the group consisting of:
   sucrose phosphorylase and maltodextrin phosphorylase.

2. The process according to claim 1, wherein said phosphoric acid is selected from the one or more of the group consisting of: phosphoric acid, metaphosphoric acid, trypoliphosphoric acid, polyphosphoric acid, diphosphoric acid, polymetaphosphoric acid and the salts thereof.

3. The process according to claim 1, wherein said phosphoric acid salt is selected from the one or more of the group consisting of: monobasic potassium phosphate, dibasic potassium phosphate, monobasic sodium phosphate and dibasic sodium phosphate.

4. The process according to claim 1, wherein said phosphoric acid is present in the medium at a concentration of from 400 mM to 1.2 M for *Leuconostoc* or from 100 mM to 600 mM for *Corynebacterium*.

5. The process according to claim 1, wherein the collecting step is performed by one or more of the following procedures selected from the group consisting of: ultrafiltration, salting-out, ion exchange, hydrophobic chromatography, gel filtration and drying.

6. A process for producing sucrose phosphorylase from *Leuconostoc*, which comprises:
   culturing *Leuconostoc* in a medium comprising from 400 mM to 1.2 M concentration of a phosphoric acid or a salt thereof, and
   collecting sucrose phosphorylase produced in the medium.

7. A process for producing maltodextrin phosphorylase from *Corynebacterium*, which comprises:
   culturing *Corynebacterium* in a medium comprising from 100 mM to 600 mM concentration of a phosphoric acid or a salt thereof, and
   collecting maltodextrin phosphorylase produced in the medium.

8. The process according to claim 6, wherein said *Leuconostoc* is selected from the group consisting of: *L. mesenteroides* JCM9693, *L. mesenteroides* KSM-SP1, *L. mesenteroides* KSM-SP78, *L. carnosum* JCM9695, *L. argentinum* JCM1 1052 and *L. pseudomesenteroides* JCM11045.

9. The process according to claim 7, wherein said *Corynebacterium* is selected from the group consisting of: *c. vitaeruminis* JCM1323, *c. callunae* IFO15359, *c. glutainicum* JCM1321 and *c. glutamicum* KSM-MP669.

* * * * *

UNITED STATES PATENT AND TRADEMARK OFFICE
CERTIFICATE OF CORRECTION

PATENT NO. : 7,413,886 B2
APPLICATION NO. : 10/558303
DATED : August 19, 2008
INVENTOR(S) : Kazuaki Igarashi et al.

It is certified that error appears in the above-identified patent and that said Letters Patent is hereby corrected as shown below:

In claim 8, column 7, line 5, change "*JCM*1 1052" to --JCM11052--.

In claim 9, column 8, line 3, change "*c. glutainicum*" to --*c. glutamicum*--.

Signed and Sealed this

Thirtieth Day of December, 2008

JON W. DUDAS
*Director of the United States Patent and Trademark Office*